(12) United States Patent
Reddy

(10) Patent No.: US 11,464,613 B2
(45) Date of Patent: Oct. 11, 2022

(54) DYNAMIC BIOMETRIC MESH

(71) Applicant: P. Pravin Reddy, Atlanta, GA (US)

(72) Inventor: P. Pravin Reddy, Atlanta, GA (US)

( * ) Notice: Subject to any disclaimer, the term of this patent is extended or adjusted under 35 U.S.C. 154(b) by 330 days.

(21) Appl. No.: 15/931,977

(22) Filed: May 14, 2020

(65) Prior Publication Data

US 2020/0268498 A1   Aug. 27, 2020

Related U.S. Application Data

(63) Continuation of application No. 14/730,723, filed on Jun. 4, 2015, now abandoned.

(60) Provisional application No. 62/008,051, filed on Jun. 5, 2014.

(51) Int. Cl.
*A61F 2/00* (2006.01)
*A61F 2/12* (2006.01)

(52) U.S. Cl.
CPC .............. *A61F 2/0063* (2013.01); *A61F 2/12* (2013.01); *A61F 2002/0068* (2013.01)

(58) Field of Classification Search
CPC ... A61F 2/0063; A61F 2/12; A61F 2002/0068
See application file for complete search history.

(56) References Cited

U.S. PATENT DOCUMENTS

| | | |
|---|---|---|
| 2,671,444 A | 3/1954 | Pease, Jr. |
| 3,272,204 A | 9/1966 | Artandi |
| 4,576,608 A | 3/1986 | Homsy |
| 5,593,441 A | 1/1997 | Lichtenstein et al. |
| 6,162,962 A | 12/2000 | Hinsch et al. |
| 6,966,918 B1 | 11/2005 | Schuldt-Hempe et al. |
| 7,614,258 B2 | 11/2009 | Cherok et al. |
| 7,789,888 B2 | 9/2010 | Bartee et al. |
| 7,906,110 B2 | 3/2011 | Chancellor et al. |
| 8,182,545 B2 | 5/2012 | Cherok et al. |
| 8,343,232 B2 | 1/2013 | Adzich et al. |
| 8,399,243 B2 | 3/2013 | Bouten et al. |
| 8,535,719 B2 | 9/2013 | Badylak et al. |
| 8,603,117 B2 | 12/2013 | Zoland et al. |
| 8,623,096 B2 | 1/2014 | Trabucco et al. |
| 2010/0318108 A1 | 12/2010 | Datta et al. |
| 2011/0092531 A1 | 4/2011 | Hamdouchi et al. |
| 2011/0257761 A1 | 10/2011 | Mortarino |
| 2013/0282035 A1 | 10/2013 | Zoland et al. |
| 2014/0148827 A1 | 5/2014 | Odermatt et al. |
| 2014/0276993 A1 | 9/2014 | Reilly et al. |
| 2015/0032135 A1 | 1/2015 | Gorman |

FOREIGN PATENT DOCUMENTS

| | | |
|---|---|---|
| CN | 203089993 | 7/2013 |
| WO | 9814134 | 4/1998 |
| WO | 2013122700 | 8/2013 |

*Primary Examiner* — Sarah A Simpson
(74) *Attorney, Agent, or Firm* — Thomas | Horstemeyer, LLP

(57) ABSTRACT

A dynamic biometric mesh (10) has a plurality of radial members (30) and a plurality of catenaries (20). Each catenary (20) extends between and is fixed to at least one pair of adjacent radial members (30). The plurality of catenaries (20) and radial members (30) form a low mass structural system arranged in an architecture configured to be structurally stable in tension and pliable for deployment and integration with biologic tissue.

47 Claims, 8 Drawing Sheets

DYNAMIC BIOMETRIC MESH

CLAIM OF PRIORITY

This is a continuation application claiming priority to U.S. Application No. 14/730,723, filed Jun. 5, 2015, entitled "Dynamic Biometric Mesh", which claims priority to U.S. Provisional Application No. 62/008,051, filed Jun. 5, 2014 entitled "Dynamic Biometric Mesh, which applications are entirely incorporated herein by reference.

TECHNICAL FIELD

The present invention relates to meshes for supporting tissues generally, more particularly, a mesh for hernia repair or breast support.

BACKGROUND OF THE INVENTION

Ventral abdominal hernias are common and associated with significant morbidity. The most common cause for ventral hernias remains previous open abdominal surgery, although prolapse via epigastric and lower abdominal muscle wall are common as well. Over 100,000 ventral hernia repairs are performed in the USA annually. Untreated abdominal hernias can result in incarceration of bowel; organ prolapse; bowel obstruction; strangulation of bowel; and even death.

Rising obesity rates have resulted in increased recurrence rates of ventral hernias reported as high as 11% following open abdominal surgical procedures Long-term prospective studies have established mesh repair of ventral hernia as superior to primary suture repair. As noted by Dr. S. Saureland, the incidence of recurrent herniation is 10-fold higher with direct repair compared to a mesh prosthesis Existing prosthetic meshes are associated with a range of problems as well, including significant recurrent rates (10-30%); fibrosis; chronic pain; stiffness of the abdominal wall; intestinal fistula; infection; recurrences; anchor point failures; thromboses; calcification; and unfavorable bowel interactions.

Existing ventral hernia mesh technologies are biased in design as static load bearing systems, and fail to account for tensional integrity, or tensegrity; a model more appropriate to biologic systems. The preference for stiff and static meshes arises from the belief that flexible meshes are prone to resulting in abdominal bulges following herniorrhaphy; however, stiff meshes fail to dissipate tensile forces across the abdominal wall and instead absorb these energies which may contribute to their ultimate failure particularly at the anchoring points. Furthermore, many meshes are composed of non-biocompatible materials and thus destined for encapsulation that promote chronic inflammatory responses at the implantation site. Many current mesh designs rely on a large mass of material resulting in thick scar formation which in turn leads to stiffness of the abdominal wall and chronic pain. Finally, no current mesh is manufactured to match the hernia defect with regard to size, mechanical profile, or consider integrating dynamic tensile property during the healing process.

The present invention disclosed herein provides a novel ventral abdominal mesh designed to address problems associated with ventral hernias that integrate the principles of tensegrity, biocompatibility, and biometric customization.

SUMMARY OF THE INVENTION

A dynamic biometric mesh has a plurality of radial members and a plurality of catenaries. Each catenary extends between and is fixed to at least one pair of adjacent radial members. The plurality of catenaries and radial members form a low mass structural system arranged in an architecture configured to be structurally stable in tension and pliable for deployment and integration with biologic tissue.

Biometric mesh further has a central region or opening from which the radial members extend outwardly to ends defining an outer perimeter. The plurality of catenaries are preferably arranged in circumferential extending rows spaced along lengths of the radial members. Adjacent circumferential extending rows are more closely spaced near the center region and increase in spacing towards the outer perimeter.

The dynamic biometric mesh of the invention has the plurality of catenaries fixed to radial members and the sag or hang between the radial members in the rage from 0, a straight line, or greater than 0 evidencing a curved hanging path. Each catenary has zero tension in a flat plane when formed as a mesh. The dynamic biometric mesh of at least one embodiment has one or more catenaries with a positive sag or hang (a), (a) being a drop or sag between a straight line passing through the fixed ends at the radial member. Preferably all of the catenaries are elastic having a defined stretch under tension. Similarly it is preferred that the radial members are elastic having a defined stretch under tension.

Ideally, the dynamic biometric mesh is conformable about a convex curvature. The dynamic biometric mesh has the outer perimeter having a plurality of attachment or anchoring points to attach the mesh to tissue. The mesh can be stretched to the attachment points to pre-tension the mesh along the attachments. The pre-tensioning of the mesh places a tension on the catenaries and wherein the catenaries achieve a tensioned equilibrium after the mesh is anchored or affixed to the tissue. The catenaries stretch under expansion or retract under contraction in relation to the movement of the tissue to which the mesh is affixed. In one embodiment, the dynamic biometric mesh has an asymmetric configuration having an upper hemisphere extending above the central opening of increased elasticity or stretch and a lower hemisphere having a reduced elasticity or stretch. The lower hemisphere has a plurality of struts, each strut extending diagonally between adjacent catenaries and adjacent radial members. The struts are preferably attached to intersections of a respective catenary and radial members. The struts of the lower hemisphere are positioned diagonally at each intersection and can be selectively removed by cutting one or more struts to tune the structure of the mesh to accommodate the tissue to which the mesh is attached.

The dynamic biometric mesh allows for at least an upper portion or hemisphere of the mesh to expand under tension at least to 150% from its as formed unattached structure. The radial members and the catenaries have the same elasticity. The struts, radial members and catenaries may have the same elasticity.

The dynamic biometric mesh of another embodiment has one or more of the plurality of catenaries formed as a shelf having a width (w) and a length (1) creating top and bottom surface areas to affix biological materials, chemicals or pharmaceuticals to enhance tissue integration. The dynamic biometric mesh can be formed by weaving monofilaments in a multi-ply configuration. The dynamic biometric mesh is a three ply configuration. Preferably, the dynamic biometric mesh can be a multi-tiered structure having two or more connected layers of mesh.

The dynamic biometric mesh redirects forces from lateral tension into rostral-caudal alignment to direct reconstitution and normalize tissue repair. The dynamic biometric mesh, as designed, distributes tension across the catenaries and radial members to dissipate dynamic forces at the anchoring points. The dynamic biometric mesh can be configured for attachment to an abdominal wall for use in repair of abdominal wall hernias or to provide dynamic stabilization and support of breast tissue. The dynamic biometric mesh can be degradably defined by the material composition to be selectively absorbed or biologically integrated into the tissue to which it is attached. The dynamic biometric mesh can be formed using one or more techniques such as cast, printed, corrugated, embossed, extruded, die cut, welded, laser etched, laser modified tissue mimetic biodynamic.

The dynamic biometric mesh can have random or preferred surface orientation and roughness. The dynamic biometric mesh can be made with intrinsic cell instruction properties engineered into fibers which make up the catenaries and radial members using laser etching. The cell instruction properties of the mesh promote incorporation of the mesh into surrounding tissues by promoting tissue ingrowth. Alternatively, or in combination with the cell instruction, the dynamic biometric mesh may also include metal salts which are incorporated into fiber of the catenaries and radial members to act as competitive inhibitors to mediators of inflammatory response. These metal salts include titanium dioxide as a competitive inhibitor of metalloprotease mediators of the inflammatory response. The dynamic biometric mesh can be conditioned with autologous mesenchymal stem cells (MSCs) derived from processed adipose tissue, and consistent with the stromal vascular fraction (SVF). The mesh can be conditioned with the MSCs in a bioreactor in advance of insertion into the hernia defect. The dynamic biometric mesh can include a matrix to enhance cell attachment, stimulate differentiation and accentuate force transduction in alignment of the cell orientation. The dynamic biometric mesh preferably is a biosynthetic composite structure customized to the subject and accelerates incorporation into adjacent tissues. The dynamic biometric mesh can be manufactured using a 3-D printing technology, wherein the mesh is made on demand and to precisely match the hernia defect in the subject based on non-invasive measurements including physical examination. The dynamic biometric mesh is formed as a broad platform of uniform isotropic distributed radial members and catenaries or struts formed by either printed, laser cut, die cut, embossed, sprayed on suitable differential electrodes to align charge, or other means. The catenaries, radial members or struts can be over sprayed with collagen, PGLA, PCL, Poly-imides, or other bio-absorbable polymers. The dynamic biometric mesh, in one or more embodiments, emulates zoomorphic design, specifically that of a spider web, and is intended to possess an open architecture thus reducing infection and inflammation. The dynamic biometric mesh has the stress or elongation characteristics of the mesh to be suited to accommodating the cyclical load bearing properties of the ventral abdominal wall and the interstices of the mesh are smaller than 12 mm or less. The dynamic biometric mesh may incorporate one or more features in cross section of a woody stem, of a plant branching interface, demonstrates regular and randomized cells, Fibonacci and ordered arrays, varying diameters and regular, ordered arrays of inner cells any of which imparting structural tension to lateral distortion without imposing material stiffness. The catenaries and radial members are preferably formed as fibers having a tensile strength in the range of 50 to 150 N/m, preferably about 100 N/m. The catenaries and radial members may have a fiber diameter of 0.2 mm or greater, preferably a fiber diameter of 0.26 mm. The dynamic biometric mesh preferably has the Young's modulus of component fibers being 34 GPa or greater. The suture pull out strength is at least 5.5 kg at the outer perimeter of the mesh.

BRIEF DESCRIPTION OF THE DRAWINGS

The invention will be described by way of example and with reference to the accompanying drawings in which.

DETAILED DESCRIPTION OF THE INVENTION

Figure 1A:
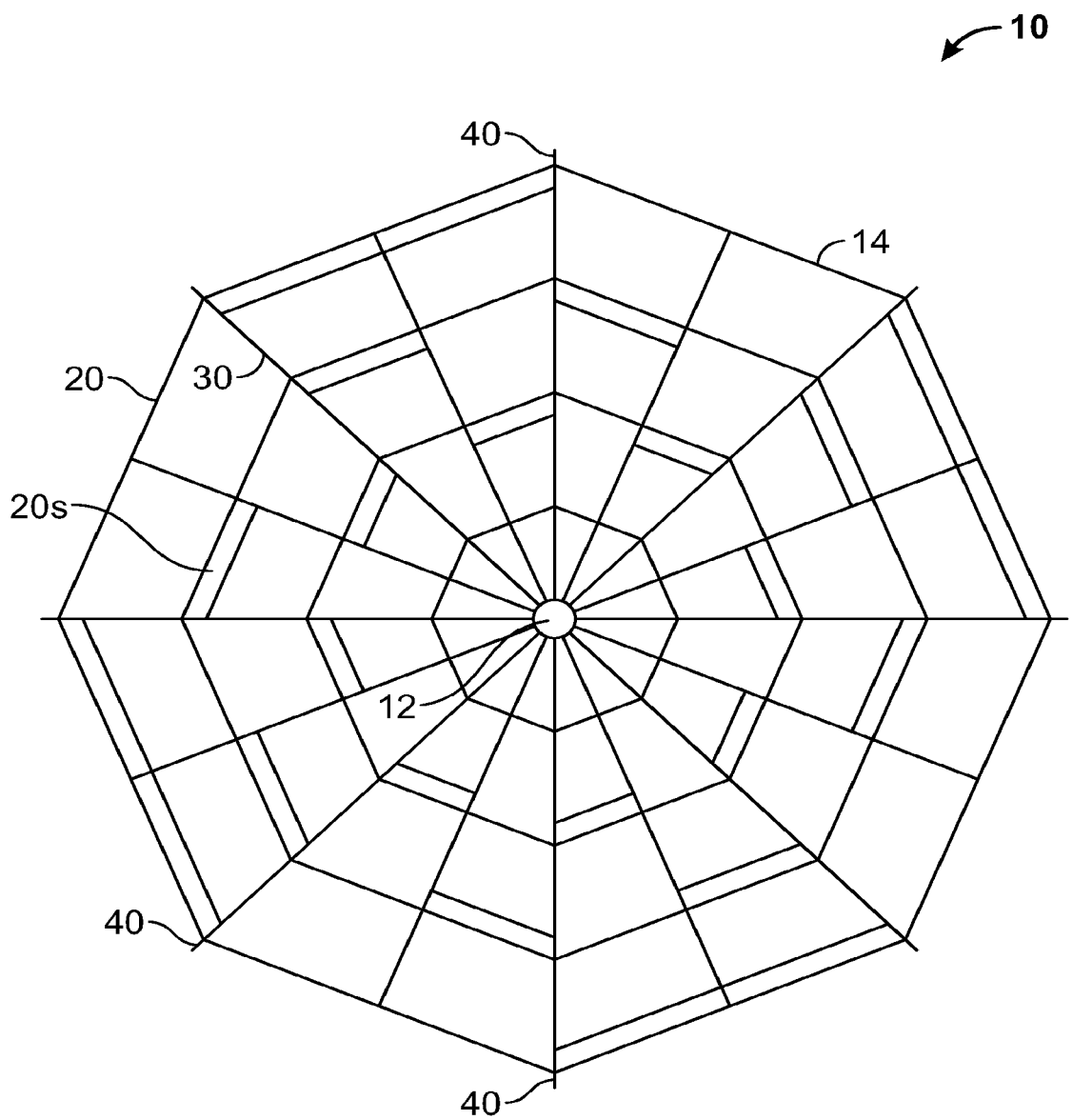
FIG. 1A is a reduced mass mesh made in accordance with a first embodiment of the invention.

The present invention employs a plurality of catenary members or fibers hereinafter called catenaries.

In physics and geometry, a catenary is the curve that an idealized hanging chain or cable assumes under its own weight when supported only at its ends. The curve has a U-like shape, superficially similar in appearance to a parabola, but it is not a parabola: it is a (scaled, rotated) graph of the hyperbolic cosine. The curve appears in the design of certain types of arches and as a cross section of the catenoid—the shape assumed by a soap film bounded by two parallel circular rings.

The catenary is also called the "alysoid", "chainette", or, particularly in the material sciences, "funicular".

Mathematically, the catenary curve is the graph of the hyperbolic cosine function. The surface of revolution of the catenary curve, the catenoid, is a minimal surface, specifically a minimal surface of revolution. The mathematical properties of the catenary curve were first studied by Robert Hooke in the 1670's, and its equation was derived by Leibniz, Huygens and Johann Bernoulli in 1691.

Catenaries and related curves are used in architecture and engineering, in the design of bridges and arches, so that forces do not result in bending moments.

Over any horizontal interval, the ratio of the area under the catenary to its length equals a, independent of the interval selected. The catenary is the only plane curve other than a horizontal line with this property. Also, the geometric centroid of the area under a stretch of catenary is the midpoint of the perpendicular segment connecting the centroid of the curve itself and the x-axis.

In an elastic catenary, the chain is replaced by a spring which can stretch in response to tension. The spring is assumed to stretch in accordance with Hooke's Law. Specifically, if p is the natural length of a section of spring, then the length of the spring with tension T applied has length $$s = \left(1 + \frac{T}{E}\right)p,$$

where E is a constant. In the catenary the value of T is variable, but ratio remains valid at a local level, so $$\frac{ds}{dp} = 1 + \frac{T}{E}.$$

The curve followed by an elastic spring can now be derived following a similar method as for the inelastic spring.

The equations for tension of the spring are $T \cos \varphi = T_0$, and $T \sin \varphi = \lambda_0 g p$, from which $$\frac{dy}{dx} = \tan\varphi = \frac{\lambda_0 g p}{T_0}, \; T = \sqrt{T_0^2 + \lambda_0^2 g^2 p^2},$$

where p is the natural length of the segment from c to r and $\lambda_0$ is the mass per unit length of the spring with no tension and g is the acceleration of gravity. Write $$a = \frac{T_0}{\lambda_0 g} \text{ so } \frac{dy}{dx} = \tan\varphi = \frac{p}{a}, \; T = \frac{T_0}{a}\sqrt{a^2 + p^2}.$$

Then $$\frac{dx}{ds} = \cos\varphi = \frac{T_0}{T} \text{ and } \frac{dy}{dx} = \sin\varphi = \frac{\lambda_0 g p}{T},$$

from which $$\frac{dx}{dp} = \frac{T_0}{T}\frac{ds}{dp} = T_0\left(\frac{1}{T} + \frac{1}{E}\right) = \frac{a}{\sqrt{a^2+p^2}} + \frac{T_0}{E}$$

$$\frac{dy}{dp} = \frac{\lambda_0 g p}{T}\frac{ds}{dp} = \frac{T_0 p}{a}\left(\frac{1}{T} + \frac{1}{E}\right) = \frac{p}{\sqrt{a^2+p^2}} + \frac{T_0 p}{Ea}.$$

Integrating gives the parametric equations $$x = a \; \mathrm{arcsinh}(p/a) + \frac{T_0}{E}p + \alpha,$$

$$y = \sqrt{a^2 + p^2} + \frac{T_0}{2Ea}p^2 + \beta.$$

Again, the x and y-axes can be shifted so $\alpha$ and $\beta$ can be taken to 0.

$$\text{So } x = \mathrm{arcsinh}(p/a) + \frac{T_0}{E}p,$$

$$y = \sqrt{a^2 + p^2} + \frac{T_0}{2Ea}p^2.$$

are parametric equations for the curve.

Chain under a general force: With no assumptions have been made regarding the force G acting on the chain, the following analysis can be made. First, let T=T(s) be the force of tension as a function of s. The chain is flexible so it can only exert a force parallel to itself. Since tension is defined as the force that the chain exerts on itself, T must be parallel to the chain. In other words, T=Tu where T is the magnitude of T and u is the unit tangent vector.

Second, let G=G(s) be the external force per unit length acting on a small segment of a chain as a function of s. The forces acting on the segment of the chain between s and s+$\Delta$s are the force of tension T(s+$\Delta$s) at one end of the segment, the nearly opposite force $-$T(s) at the other end, and the external force acting on the segment which is approximately G$\Delta$s. These forces must balance so T(s+$\Delta$s)$-$T(s)+G$\Delta$s$\approx$0. Divide by $\alpha$s and take the limit as $\Delta$s$\rightarrow$0 to obtain $$\frac{dT}{ds} + G = 0.$$

These equations can be used as the starting point in the analysis of a flexible chain acting under any external force. In the case of the standard catenary, G=(0, $-\lambda$g) where the chain has mass $\lambda$ per unit length and g is the acceleration of gravity.

In the present invention, each catenary can have or exhibit a linear path connected at two fixed points on the pair of radially adjacent members. In this case, the catenary is not curved, but its elasticity transmits the tension forces along the stretched path parallel to the catenary. Exactly as found mathematically above. Interestingly, the elastic or curved catenary system is an ideal structure for affixing to a three-dimensional surface like a sphere or any convex shape as it conforms elegantly about the curvature. Ideally, the curved catenaries have a smaller hang at the origin and increase in hang at the radial extremes. This allows for the increased expansion outward of the convexity prior to tensioning the mesh system. When affixed or anchored to the tissue, the radial members and catenaries can be tensioned and the tension will be parallel to the member's path and redirected along attached catenaries.

Biologic systems have a component of load bearing and tensional integrity or tensegrity. Many static structures designed to repair or replace biologic structures are purely load bearing in nature and therefore destined to fail as they cannot replicate the varying tensions the abdominal wall cycles through thousands of time daily. For example, the Law of Laplace predicts abdominal wall tension is a dependent variable of abdominal wall radius. The radius of the abdomen varies many times daily with breathing, coughing, and locomotion resulting in varying abdominal wall tensions. In fact, it has been reported that the ventral abdominal fascia elongates up to 150% of resting length during exercise. As such, the ventral abdominal wall cannot therefore be treated as a static structure in which a defect can be repaired with a static mesh.

Tissue incompatibility results from the lack of incorporation into adjacent tissues of current prostheses. Since the prosthesis cannot be incorporated, a foreign body reaction results and leads to encapsulation by fibrous tissue as the body attempts to sequester the foreign material. While fibrous tissue effectively separates and hides the tissue, the inter-fragmentary strain of dissimilar tissues results in chronic irritation, fibrous proliferation and sustained inflammation. Under this biologic strain, the capsule in turn can harbor bacteria resulting in chronic infections and inflammatory response.

Biometric analysis of abdominal wall defects currently documents the defect in 2-dimensions, chiefly with imaging and physical exam. The shortcoming does not take into account differential abdominal wall tensions that vary between the separate anatomic zones of the abdominal wall. For instance, none of the current models recognize that the lower abdomen generates greater tension in comparison with the upper abdomen. Taking into consideration differential abdominal wall tensions, extant technologies can potentially integrate anatomic distinctions of individual patients and offer insight into biomechanics thus permitting the design of customized meshes from basic stock designs.

Current hernia meshes are non-customized prosthetic devices. The present invention allows a customized prosthesis to be fabricated based on biometric analysis of the subject.

Anchor point failures are a common cause for hernia failures. Most anchoring techniques in open hernia failure rely on horizontally applied sutures which necessarily cause tissue strangulation and ischemia. The ischemic tissue results in loosening of the anchoring sutures and failure of the fixation point. The current mesh design may be anchored using traditional suture techniques or even more advanced fixation techniques.

Meshes composed of acellular dermal matrix (ADM) are purported to result in tissue regeneration but suffer rapid decline of tensile strength which fails to account for efficacy in herniorrhaphy. Furthermore, ADMs probably do not undergo the degree of tissue incorporation and neo-vascularization envisioned by manufacturers/vendors.

Figure 5:
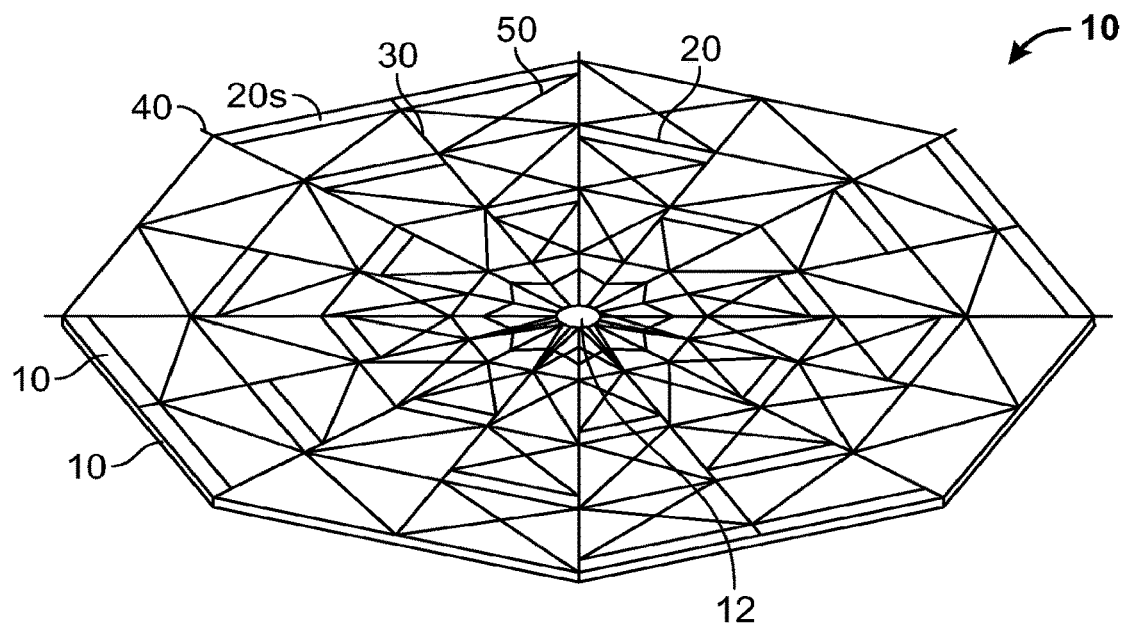
FIG. 5 is a multi-layered mesh.

As shown in FIGS. 1-7, the proposed mesh 10 is engineered with intrinsic elastomeric properties and comprised of a system of catenaries 20 and trusses or radial members 30, that might be additive, channeled, cast, printed, corrugated, embossed, extruded, die cut, welded, laser etched, laser modified, mimetic in origin, biodynamic, and incorporate random and preferred surface orientation and roughness intended to actuate and amplify defined stresses within a range of tensile and compressive forces that are known to be structurally stable in tension and yet sufficiently pliable for deployment and integration of biologic tissues; particularly those of the abdominal wall. Biometric mesh 10 further has a central region or opening 12 from which the radial members 30 extend outwardly to ends defining an outer perimeter 14. The arrangement of components serves to distribute tension across the hernia defect as well as to dissipate dynamic forces to the anchoring points 40. The addition of struts 50, shown in FIGS. 2-4, to select areas of the mesh 10 can adjust the tensile properties of the prostheses to better accommodate the native tensile properties of the implant site. The mesh 10 can be composed of separate and numerous layers that are connected and juxtaposed to inhibit strain and protect the structural integrity, as shown in FIG. 5. In preferred embodiment, forces will be redirected from lateral tension into rostral-caudal alignment to direct reconstitution and normalize anatomical repair of the linea alba.

Elastomeric properties of the mesh 10 can be engineered into the mesh 10 as result of weaving static monofilament materials in a three-ply configuration. Use of monofilament materials reduce the interstices available for seeding with bacterial contaminants.

Intrinsic cell instruction properties can be engineered into the mesh fibers using laser etching. The cell instruction properties of the mesh promotes incorporation of the prostheses into surrounding tissues by promoting tissue ingrowth.

Metal salts incorporated into the mesh fiber act as competitive inhibitors to mediators of inflammatory response. These could include titanium dioxide as a competitive inhibitor of metalloprotease mediators of the inflammatory response (Spyros AS, 2013).

In one instance, the proposed mesh 10 is conditioned with autologous mesenchymal stem cells (MSCs) derived from processed adipose tissue, and consistent with the stromal vascular fraction (SVF).

The mesh 10 is preferably conditioned with the MSCs in a bioreactor in advance of insertion into the hernia defect. It is well known in the art that matrix coating enhances cell attachment, stimulates differentiate, and accentuates force transduction in alignment of the cell orientation. The biosynthetic composite structure can be customized to the subject and accelerates incorporation into adjacent tissues. It is envisioned that the mesh 10 will ultimately be incorporated by organized tissue aligned and modeled with the tensile forces that the mesh is continually subject to. Conditioning of the mesh 10 with MSC will reduce fibrosis and potentially decrease bowel interactions such as adhesions.

The mesh 10 can be manufactured using a 3-D printing technology and can therefore be made on demand and to precisely match the hernia defect in the subject based on non-invasive measurements including physical exam.

In addition to a process of additive fabrication (3D-Printing), it is also conceivable that a broad platform of uniform isotropic distributed struts and trusses would be printed, laser cut, die cut, embossed, sprayed on suitable differential electrodes to align charge, or other means with these as example.

The struts 50 might also be over sprayed with collagen, PGLA, PCL, Poly-imides, or other bio-absorbable polymers known in the art.

Among other defined structures, the mesh 10 emulates zoomorphic design, specifically that of a spider web, and is intended to possess an open architecture thus reducing infection and inflammation. In this manner a reduced-mass mesh 10 results. The stress/elongation characteristics of woven spider silk are particularly well suited to accommodating the cyclical load bearing properties of the ventral abdominal wall. Small pore size is associated with increased rates of infection. The interstices of the proposed mesh are smaller than 12 mm or less than the minimal reported size fora Richter's hernia.

Still other biomimetic designs would include those elaborated in cross section of woody stems, of plant branching interfaces, demonstrating regular and randominzed cells, fibonacci and ordered arrays, varying diameters and regular, ordered arrays of inner cells that impart structural tension to lateral distortion without imposing material stiffness.

Other potential elaborations of the design might be defined as mathematical roulette curves of the variety technically known as hypotrochoids and epitrochoids (similar to spirograph; images/figures at the end. Example of such alternative designs are found in FIGS. 2-4.

Figure 1B:
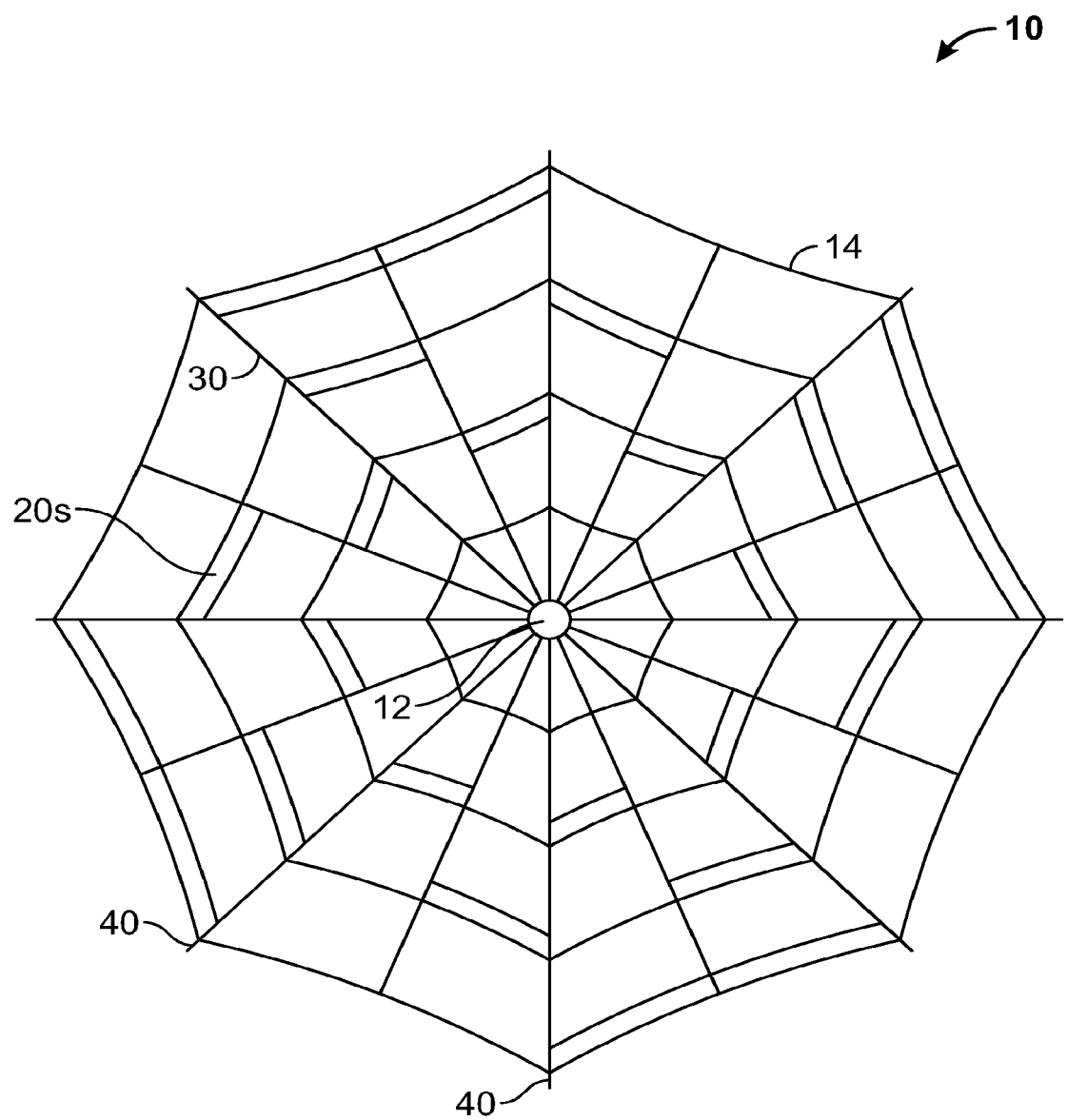
FIG. 1B is the same mesh as FIG. 1A wherein the catenaries are curved, each being suspended between two points on pairs of radial members.
Figure 2:
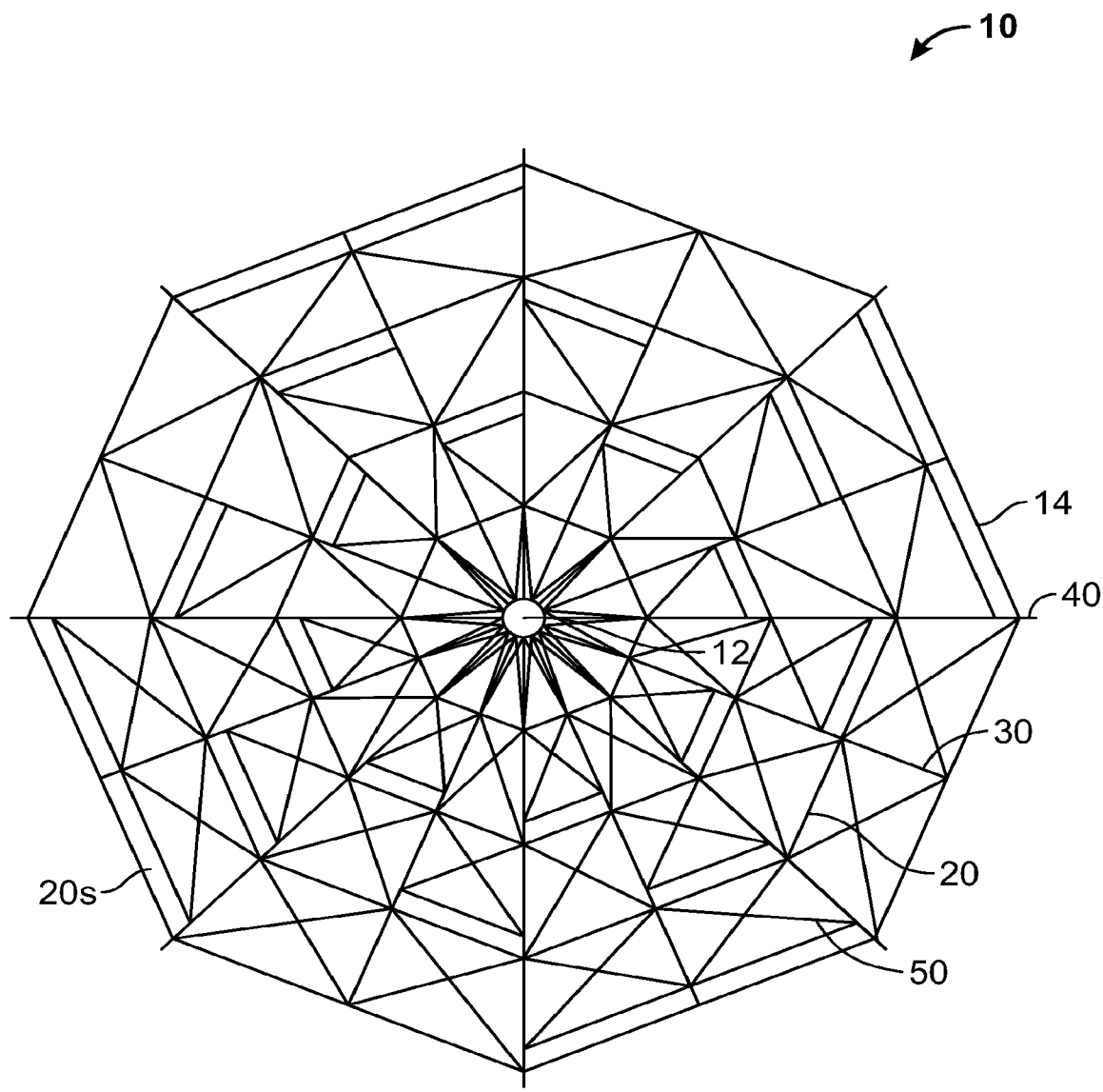
FIG. 2 is a second embodiment mesh with stiffening struts.
Figure 3:
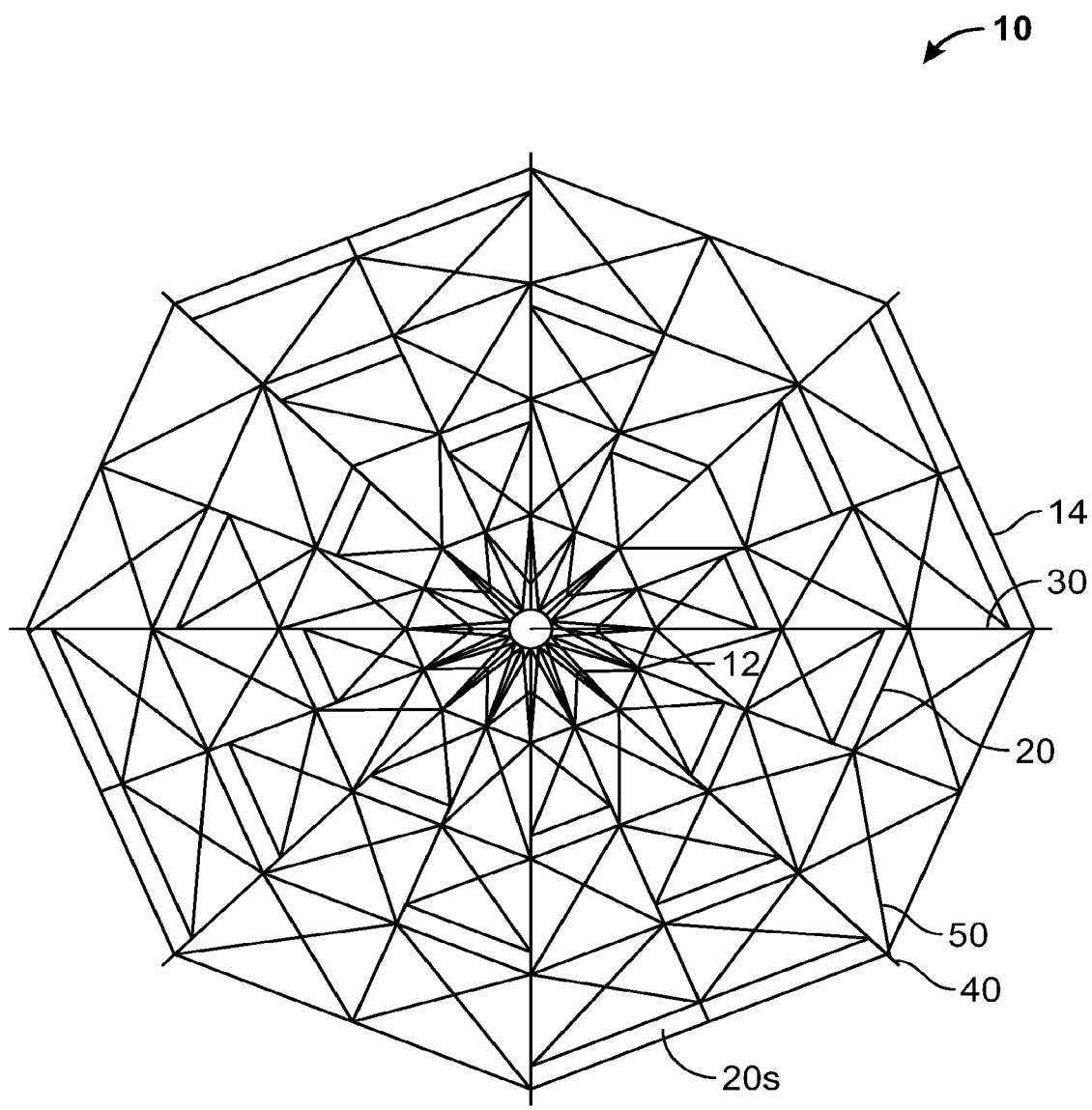
FIG. 3 is a third embodiment with an alternative mesh design.
Figure 4:
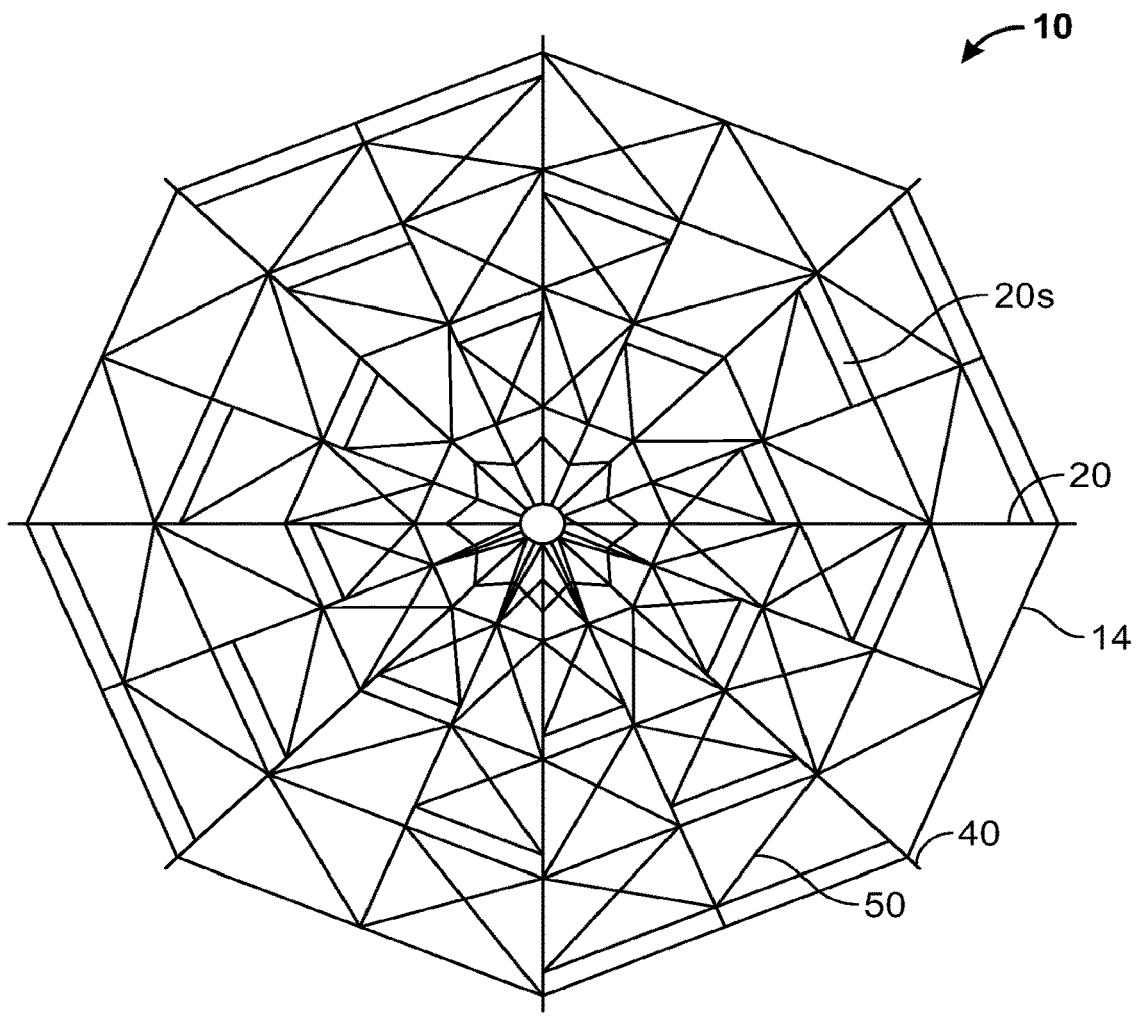
FIG. 4 is a fourth embodiment alternative mesh design.

As shown in FIG. 1, some of the catenaries 20 may be formed as shelves 20S or trays 20 with surface undulations, mimetic grooves, instructive and resonant surface effects can be incorporated into the mesh 10 at regular intervals in order to provide a purchase for MSCs and to serve as an initial nidus from where proliferation can occur to seed the entirety of the mesh 10. It is not believed that a confluence of cell matrix is necessary prior to implantation, and disclose that the wound milieu, including growth factors, stem cells, cytokines, and inflammatory priming are all possible events. Accentuating the potential to define matrix deposition as an adjunct resonating dynamic integration of loading bears the dividend of design.

The tensile strength of the mesh fibers is preferably between 50 and 150 N/m, preferably about 100 N/m. The maximum tension generated across the abdominal wall is reported to be 32 N/m Fiber diameter is 0.2 mm or greater, typically about 0.26 mm.

Young's modulus of component fibers is anticipated to be 34 GPa.

Suture pull out strength is at least 5.5 kg at the periphery or perimeter 14 of the mesh 10 at the anchor points 40.

Figure 6:
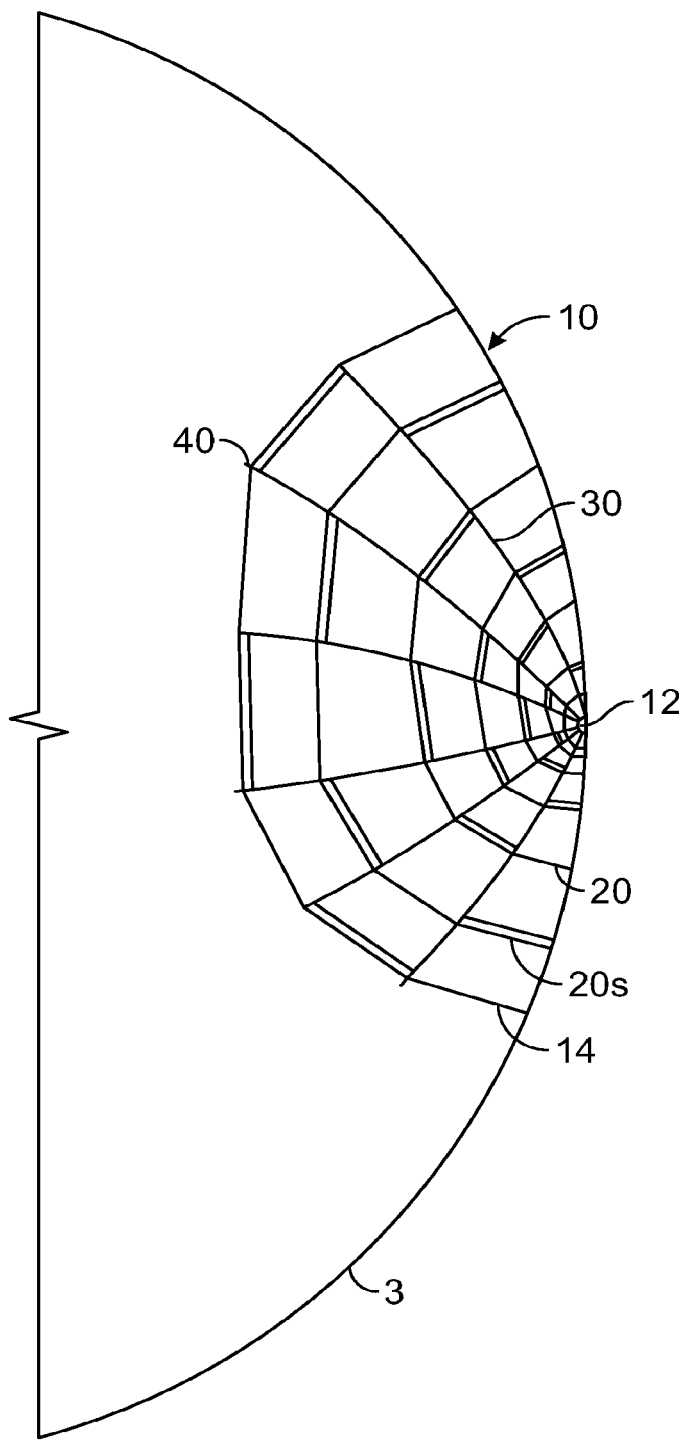
FIG. 6 is a depiction of the mesh on a convex surface.

As shown in FIG. 6, the dynamic mesh 10 is shown overlying a convex surface 3 replicating an abdomen having a typical rounded or domed curvature. As shown, the mesh 10 will conform easily to this surface, and does so with little or no effort due to its compliant nature. This is not possible with woven screen like mesh.

Figure 7A:
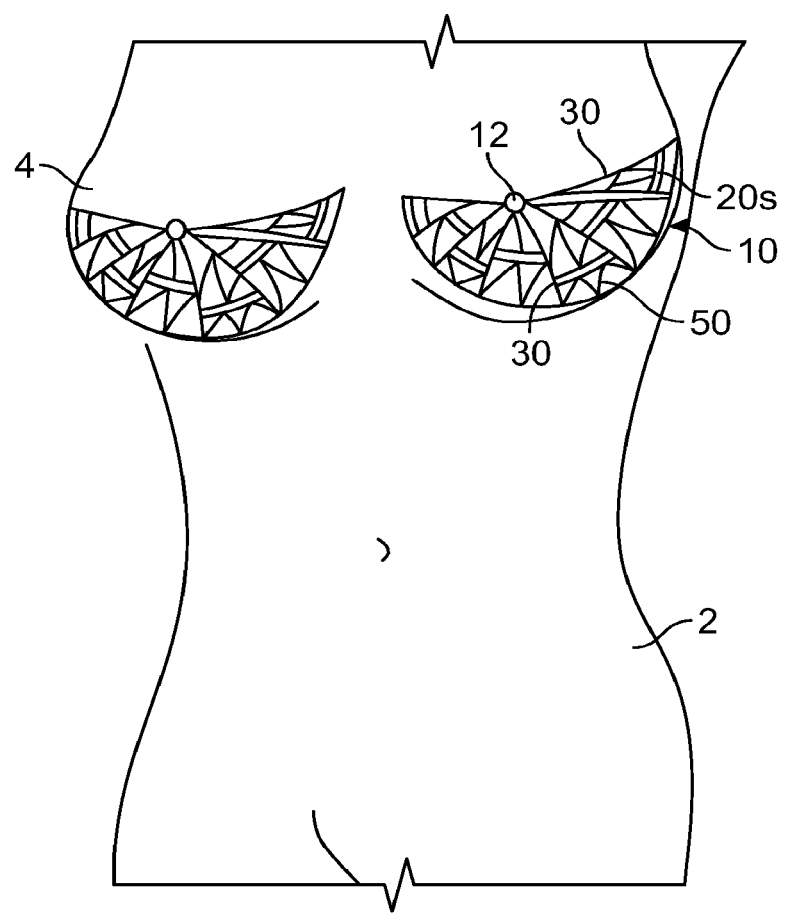
FIGS. 7A and 7B are a fifth embodiment mesh for use in breast surgery as a breast support structure.
Figure 7B:
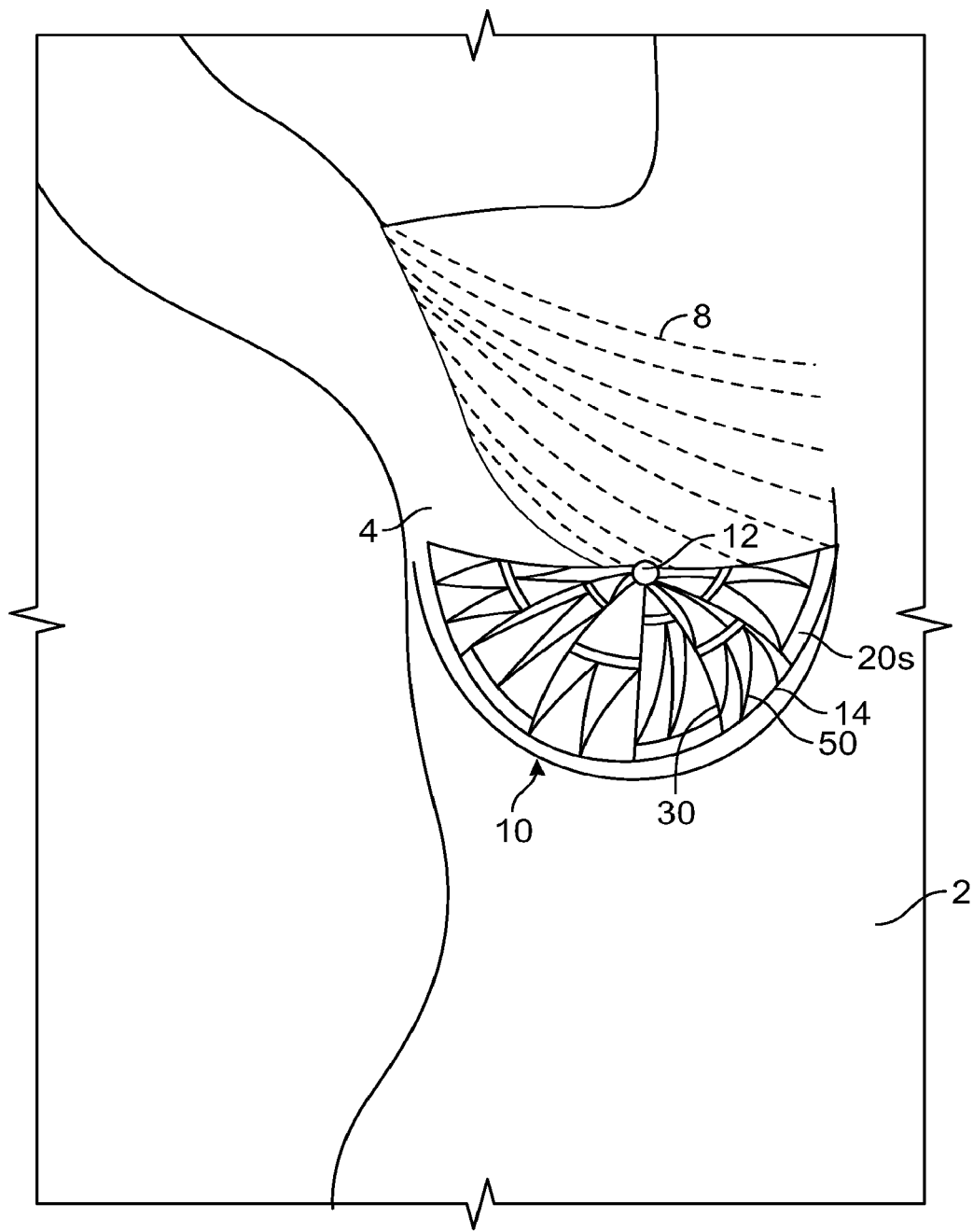

In FIGS. 7A and 7B, an alternative mesh 10 is shown. The mesh 10 is ideally suited to support a patient's 2 breast 4 by being affixed to the lower portion of the tissue. As shown, the mesh 10 is made having half the structure of a hernia mesh 10, preferably the lower portion or lower hemisphere. Alternatively, this construct can be achieved by folding the mesh 10 of any of the previous figures to create a double layer of mesh.

The mesh 10 is best applied to reconstruct the inferior, or lower, pole of the breast 4. In this position, it can support an implant or native breast tissue thus opposing gravitational descent of an implant or breast tissue. When the implant 10 is placed in the sub-pectoral plane, as is popular in breast reconstruction or augmentation, the tensegrity structure allows the implant 10 to migrate with activation of the pectoralis muscle 8 but the implant 10 would "spring" back when the pectoralis 8 is relaxed.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

The invention claimed is:

1. A dynamic biometric mesh comprising:
a plurality of radial members;
a plurality of catenaries, each catenary extending between at least one pair of adjacent radial members and fixed to the at least one pair of adjacent radial members at fixed ends;
a central opening from which the radial members extend outwardly to ends defining an outer perimeter; and
a plurality of discrete diagonal struts selectively positioned in open areas of the mesh defined by a configuration of the radial members and catenaries, individual discrete diagonal struts of the plurality of discrete diagonal struts extending diagonally between (1) a respective first intersection of a respective first catenary and a respective first radial member and (2) a respective second intersection of a respective second catenary and a respective second radial member, the respective first catenary being adjacent to the respective second catenary, the respective first radial member being adjacent to the respective second radial member, and a respective position of the individual discrete diagonal struts being selected to adjust tensile properties of the mesh to accommodate the native tensile properties of biologic tissue,
wherein the mesh has an asymmetric configuration having an upper hemisphere extending above the central opening and a lower hemisphere below the central opening, the plurality of discrete diagonal struts being positioned in the lower hemisphere,
wherein the upper hemisphere has an increased elasticity as compared to the lower hemisphere,
wherein the plurality of catenaries and radial members form a low mass structural system arranged in an architecture configured to be structurally stable in tension and pliable for deployment and integration with the biologic tissue, and
wherein the mesh is a biosynthetic composite structure customized for a specific subject based on the selective positioning of the plurality of discrete diagonal struts and configured to accelerate incorporation into adjacent tissues.

2. The dynamic biometric mesh of claim 1, wherein the plurality of catenaries are arranged in adjacent circumferential extending rows spaced along lengths of the radial members.

3. The dynamic biometric mesh of claim 2, wherein the adjacent circumferential extending rows are more closely spaced near the center opening and increase in spacing towards the outer perimeter.

4. The dynamic biometric mesh of claim 2, wherein the outer perimeter has a plurality of attachment points configured to attach the mesh to tissue.

5. The dynamic biometric mesh of claim 4, wherein the mesh can be stretched to the attachment points to pre-tension the mesh along the attachment points.

6. The dynamic biometric mesh of claim 5, wherein the pre-tensioning of the mesh places a tension on the catenaries and wherein the catenaries achieve a tensioned equilibrium after being affixed.

7. The dynamic biometric mesh of claim 6, wherein the catenaries stretch under expansion or retract under contraction in relation to a movement of a tissue to which the mesh is configured to be affixed.

8. The dynamic biometric mesh of claim 7, wherein the upper hemisphere of the mesh can expand under tension to at least 150%.

9. The dynamic biometric mesh of claim 8, wherein the radial members and the catenaries have the same elasticity.

10. The dynamic biometric mesh of claim 4, wherein the mesh distributes tension across the catenaries and radial members to dissipate dynamic forces at the attachment points.

11. The dynamic biometric mesh of claim 9, wherein a suture pull out strength is at least 5.5 kg at the outer perimeter of the mesh.

12. The dynamic biometric mesh of claim 1, wherein each of the plurality of catenaries is fixed to at least one of the plurality of radial members and a sag or hang between the radial members is in a range from 0, a straight line, to greater than 0, evidencing a curved hanging path, each catenary having zero tension in a flat plane when formed as the mesh.

13. The dynamic biometric mesh of claim 1, wherein at least one of the plurality of catenaries has a positive sag or hang between a straight line passing through the fixed ends at the radial members.

14. The dynamic biometric mesh of claim 1, wherein the catenaries are elastic having a defined stretch under tension.

15. The dynamic biometric mesh of claim 1, wherein the radial members are elastic having a defined stretch under tension.

16. The dynamic biometric mesh of claim 1, wherein the mesh is conformable about a convex curvature.

17. The dynamic biometric mesh of claim 1, wherein the discrete diagonal struts, radial members and catenaries have the same elasticity.

18. The dynamic biometric mesh of claim 1, wherein at least one of the plurality of discrete diagonal struts can be selectively removed by cutting the at least one discrete diagonal strut to tune the mesh to accommodate a tissue to which the mesh is configured to be attached.

19. The dynamic biometric mesh of claim 1, wherein one or more of the plurality of catenaries is formed as a shelf having a width (w) and a length (l) creating top and bottom surface areas to affix biological materials, chemicals or pharmaceuticals to enhance tissue integration.

20. The dynamic biometric mesh of claim 1, wherein the mesh is formed by weaving monofilaments in a multi-ply configuration.

21. The dynamic biometric mesh of claim 20, wherein the mesh is a three ply configuration.

22. The dynamic biometric mesh of claim 1, wherein the mesh redirects forces from lateral tension into rostral-caudal alignment to direct reconstitution and normalize tissue repair.

23. The dynamic biometric mesh of claim 1, wherein the mesh is a multi-tiered structure having two or more connected layers of mesh.

24. The dynamic biometric mesh of claim 1, wherein the mesh is configured for attachment to an abdominal wall for use in repair of abdominal wall hernias.

25. The dynamic biometric mesh of claim 1, wherein the mesh is configured to provide dynamic stabilization and support of breast tissue.

26. The dynamic biometric mesh of claim 1, wherein a material composition of the mesh is degradably defined to be selectively absorbed or biologically integrated into a tissue to which it is configured to be attached.

27. The dynamic biometric mesh of claim 1, wherein the mesh is formed using one or more techniques such as cast, printed, corrugated, embossed, extruded, die cut, welded, laser etched, laser modified tissue mimetic biodynamic or any combination thereof.

28. The dynamic biometric mesh of claim 26, wherein the mesh has random or preferred surface orientation and roughness.

29. The dynamic biometric mesh of claim 1, wherein intrinsic cell instruction properties are engineered into fibers which make up the catenaries and radial members using laser etching, the cell instruction properties of the mesh promoting incorporation of the mesh into surrounding tissues by promoting tissue ingrowth.

30. The dynamic biometric mesh of claim 1, wherein metal salts are incorporated into fiber of the catenaries and radial members to act as competitive inhibitors to mediators of inflammatory response.

31. The dynamic biometric mesh of claim 30, wherein the metal salts include titanium dioxide as a competitive inhibitor of metalloprotease mediators of the inflammatory response.

32. The dynamic biometric mesh of claim 1, wherein the mesh is conditioned with autologous mesenchyrnal stem cells (MSCs) derived from processed adipose tissue, and consistent with the stromal vascular fraction (SVF).

33. The dynamic biometric mesh of claim 32, wherein the mesh is conditioned with the MSCs in a bioreactor in advance of being configured to be attached to a tissue.

34. The dynamic biometric mesh of claim 33, wherein the mesh has a matrix to enhance cell attachment, stimulate differentiation and accentuate force transduction in alignment of a cell orientation.

35. The dynamic biometric mesh of claim 1, wherein the mesh is manufactured using a 3-D printing technology, and wherein the mesh is made on demand and to precisely match a hernia defect in a subject based on non-invasive measurements including physical examination.

36. The dynamic biometric mesh of claim 1, wherein the mesh is formed as a broad platform of uniform isotropic distributed radial members and catenaries or struts formed by being printed, laser cut, die cut, embossed, or sprayed on suitable differential electrodes to align charge.

37. The dynamic biometric mesh of claim 36, wherein the catenaries, radial members, or struts are over sprayed with collagen, PGLA, PCL, Poly-imides, or other bio-absorbable polymers.

38. The dynamic biometric mesh of claim 1, wherein the mesh emulates zoomorphic design, specifically that of a spider web, and is intended to possess an open architecture thus reducing infection and inflammation.

39. The dynamic biometric mesh of claim 38, wherein stress or elongation characteristics of the mesh are suited to accommodating cyclical load bearing properties of a ventral abdominal wall and one or more interstices of the mesh are smaller than 12 mm or less.

40. The dynamic biometric mesh of claim 1, wherein the mesh incorporates one or more features in a cross section of a woody stem, of a plant branching interface, demonstrates regular and randomized cells, Fibonacci and ordered arrays, varying diameters and regular, ordered arrays of inner cells any of which imparting structural tension to lateral distortion without imposing material stiffness.

41. The dynamic biometric mesh of claim 1, wherein a tensile strength of the catenaries or radial members is in a range of 50 to 150 N/m.

42. The dynamic biometric mesh of claim 41, wherein the tensile strength of the catenaries or radial members are formed as fibers having a tensile strength of 100 N/m.

43. The dynamic biometric mesh of claim 1, wherein the catenaries and radial members have a fiber diameter of 0.2 mm or greater.

44. The dynamic biometric mesh of claim 43, wherein the catenaries and radial members have a fiber diameter of 0.26 mm.

45. The dynamic biometric mesh of claim 41, wherein the Young's modulus of the catenaries and radial members is 34 GPa or greater.

46. The dynamic biometric mesh of claim 1, wherein a first catenary is elastic and is fixed between a first radial member and a second radial member of the plurality of radial members, the first catenary being elastic and straight.

47. The dynamic biometric mesh of claim 1, wherein at least a portion of the catenaries comprise a respective shelf with at least one of surface undulations, mimetic grooves, instructive surface effects, or resonant surface effects.

* * * * *